United States Patent [19]
Fleury et al.

[11] Patent Number: 5,969,623
[45] Date of Patent: *Oct. 19, 1999

[54] GAS ALARM

[75] Inventors: Byron Fleury; Andrew Stanton, both of Saint James, N.Y.

[73] Assignee: Marketspan Corporation, Hicksville, N.Y.

[ * ] Notice: This patent is subject to a terminal disclaimer.

[21] Appl. No.: 08/998,086

[22] Filed: Dec. 24, 1997

Related U.S. Application Data

[63] Continuation of application No. 08/631,642, Apr. 10, 1996.

[51] Int. Cl.$^6$ ..................................................... G08B 17/10
[52] U.S. Cl. ........................... 340/632; 340/633; 340/634; 73/23.2; 73/23.31; 702/24
[58] Field of Search ..................................... 340/632, 633, 340/634; 73/23.2, 23.31, 25.01, 31.05, 31.06; 364/550, 496; 422/94, 98; 702/24

[56] References Cited

U.S. PATENT DOCUMENTS

| | | |
|---|---|---|
| 3,420,636 | 1/1969 | Robbins . |
| 3,518,058 | 6/1970 | Slater . |
| 3,549,327 | 12/1970 | Fergusson . |
| 3,577,222 | 5/1971 | Ward . |
| 3,662,171 | 5/1972 | Brengman et al. . |
| 3,692,492 | 9/1972 | Poli, Jr. et al. . |
| 3,695,848 | 10/1972 | Taguchi . |
| 3,786,462 | 1/1974 | Hayden . |
| 3,865,550 | 2/1975 | Bott et al. . |
| 3,871,827 | 3/1975 | Seiler et al. . |
| 3,873,267 | 3/1975 | Swartz . |
| 3,879,717 | 4/1975 | Gruensfelder . |
| 3,879,985 | 4/1975 | Maslen . |
| 3,909,816 | 9/1975 | Teeters . |
| 3,927,979 | 12/1975 | Byrne et al. . |
| 3,955,929 | 5/1976 | Kawakami et al. . |
| 3,970,431 | 7/1976 | Wise . |
| 3,982,879 | 9/1976 | Pfefferle . |
| 3,997,387 | 12/1976 | Betz et al. . |
| 4,000,089 | 12/1976 | Senda . |
| 4,001,756 | 1/1977 | Heijne . |
| 4,012,692 | 3/1977 | Eicker . |
| 4,030,887 | 6/1977 | Poli et al. . |
| 4,112,356 | 9/1978 | Toy . |
| 4,198,850 | 4/1980 | Firth et al. . |
| 4,221,206 | 9/1980 | Haas et al. . |

(List continued on next page.)

FOREIGN PATENT DOCUMENTS

| 8501351 | 3/1985 | WIPO . |

OTHER PUBLICATIONS

Kirk–Othmer, Encyclopedia of Chemical Technology, Third Edition, vol. 15, John Wiley & Sons, New York (1981), pp. 638–669.

*Primary Examiner*—Jeffery A. Hofsass
*Assistant Examiner*—Julie B. Lieu
*Attorney, Agent, or Firm*—Dilworth & Barrese

[57] ABSTRACT

A gas detector is disclosed which includes a CO sensor and a processor. The CO sensor senses an environmental CO concentration and provides a variable electrical output in response. The processor receives digitized samples of the sensor's electrical output and computes, with each measurement sample, a COHb level of a hypothetical person exposed to the CO concentration sensed. The computation involves determining an equilibrium COHb level for each measurement sample, which is compared with a previously computed COHb level associated with previously measured samples. The previously computed COHb level is updated based on the comparison. When the computed COHb level is above a predetermined danger threshold, the processor preferably causes an audible and visual alarm to be activated to alert any persons present. The gas detector can further include a $CH_4$ sensor coupled to the processor for independently sensing $CH_4$ levels such that an alarm is activated when the $CH_4$ levels are above a predefined threshold. A hydrophobic zeolite filter is disposed on the sensor elements of one or both of the CO and $CH_4$ sensors to prevent erroneous readings.

17 Claims, 8 Drawing Sheets

U.S. PATENT DOCUMENTS

| | | |
|---|---|---|
| 4,221,827 | 9/1980 | Parry et al. . |
| 4,223,550 | 9/1980 | Takama et al. . |
| 4,224,280 | 9/1980 | Takama et al. . |
| 4,244,918 | 1/1981 | Yasuda et al. . |
| 4,251,225 | 2/1981 | Handa et al. . |
| 4,256,563 | 3/1981 | Goodson et al. . |
| 4,256,694 | 3/1981 | McAllister et al. . |
| 4,258,985 | 3/1981 | Yasuda et al. . |
| 4,277,439 | 7/1981 | Yasuda et al. . |
| 4,294,801 | 10/1981 | Segawa et al. . |
| 4,322,383 | 3/1982 | Yasuda et al. . |
| 4,325,912 | 4/1982 | Sawa et al. . |
| 4,327,054 | 4/1982 | Yasuda et al. . |
| 4,329,870 | 5/1982 | Farmer . |
| 4,347,732 | 9/1982 | Leary . |
| 4,378,691 | 4/1983 | Terada et al. . |
| 4,397,888 | 8/1983 | Yannopoulos et al. . |
| 4,399,684 | 8/1983 | Advani et al. . |
| 4,421,720 | 12/1983 | Kamiya et al. . |
| 4,443,791 | 4/1984 | Risgin et al. ............................ 340/634 |
| 4,443,793 | 4/1984 | Hall, Jr. . |
| 4,446,718 | 5/1984 | Bukowiecki et al. . |
| 4,457,161 | 7/1984 | Iwanaga et al. . |
| 4,458,242 | 7/1984 | Kusanagi et al. . |
| 4,482,635 | 11/1984 | Herskovitz et al. . |
| 4,489,239 | 12/1984 | Grant et al. . |
| 4,490,715 | 12/1984 | Kusanagi et al. . |
| 4,498,330 | 2/1985 | Hosoya . |
| 4,507,643 | 3/1985 | Sunano et al. . |
| 4,526,028 | 7/1985 | Hübner . |
| 4,535,315 | 8/1985 | Sakai . |
| 4,543,273 | 9/1985 | Handa et al. . |
| 4,567,475 | 1/1986 | Bukowiecki et al. . |
| 4,569,826 | 2/1986 | Shiratori et al. . |
| 4,586,143 | 4/1986 | Kaneyasu et al. . |
| 4,591,414 | 5/1986 | Zaromb et al. . |
| 4,606,219 | 8/1986 | Bout et al. . |
| 4,617,277 | 10/1986 | Bohl . |
| 4,638,443 | 1/1987 | Kaneyasu et al. . |
| 4,644,333 | 2/1987 | Barendsz et al. . |
| 4,668,635 | 5/1987 | Forster . |
| 4,670,405 | 6/1987 | Stetter et al. . |
| 4,708,941 | 11/1987 | Giuliani . |
| 4,730,479 | 3/1988 | Pyke et al. . |
| 4,732,738 | 3/1988 | Nakatani et al. . |
| 4,779,078 | 10/1988 | Ciolli . |
| 4,792,433 | 12/1988 | Katsura et al. . |
| 4,803,052 | 2/1989 | Abromaitis et al. . |
| 4,847,783 | 7/1989 | Grace et al. . |
| 4,860,223 | 8/1989 | Grilk ........................................ 364/550 |
| 4,860,573 | 8/1989 | Barendz et al. . |
| 4,870,025 | 9/1989 | Hurley et al. . |
| 4,871,916 | 10/1989 | Scott . |
| 4,896,143 | 1/1990 | Dolnick et al. . |
| 4,907,441 | 3/1990 | Shurmer . |
| 4,911,892 | 3/1990 | Grace et al. . |
| 4,944,273 | 7/1990 | Baresel et al. . |
| 5,012,671 | 5/1991 | Yagawara et al. . |
| 5,018,380 | 5/1991 | Zupancic et al. . |
| 5,034,725 | 7/1991 | Sorensen . |
| 5,061,447 | 10/1991 | Ono . |
| 5,062,065 | 10/1991 | Lampe . |
| 5,086,286 | 2/1992 | Yasukawa et al. . |
| 5,132,231 | 7/1992 | Youngs et al. . |
| 5,184,500 | 2/1993 | Krema et al. . |
| 5,221,517 | 6/1993 | Takada . |
| 5,250,169 | 10/1993 | Logothetis et al. . |
| 5,252,292 | 10/1993 | Hirata et al. . |
| 5,302,350 | 4/1994 | Goswami et al. . |
| 5,304,976 | 4/1994 | Ono . |
| 5,311,851 | 5/1994 | Wright, Jr. . |
| 5,335,534 | 8/1994 | Wong . |
| 5,346,671 | 9/1994 | Goswami et al. . |
| 5,362,651 | 11/1994 | Soltis et al. . |
| 5,400,643 | 3/1995 | DeAngelis et al. . |
| 5,405,583 | 4/1995 | Goswami et al. . |
| 5,417,821 | 5/1995 | Pyke . |
| 5,421,192 | 6/1995 | Henry . |
| 5,439,580 | 8/1995 | Akbar et al. . |
| 5,447,054 | 9/1995 | Modica et al. . |
| 5,526,280 | 6/1996 | Consadori et al. . |
| 5,764,150 | 6/1998 | Fleury et al. ............................ 340/632 |

| $CO_{ppm}$ | Linear Approximation Function For % $COH_b$ Rate of Increase |
|---|---|
| 100 | 0.1111t |
| 200 | 0.2857t |
| 300 | 0.4525t |
| 400 | 0.6667t |
| 600 | 1.0417t |
| 800 | 1.4284t |

FIG. 4

GAS ALARM

This is a continuation of copending application Ser. No. 08/631,642 filed Apr. 10, 1996, which is incorporated herein by reference.

FIELD OF THE INVENTION

This invention relates generally to carbon monoxide (CO) and methane (CH4) gas detectors and, more particularly, to a $CH_4$/CO gas detector and alarm suitable for residential use.

BACKGROUND OF THE INVENTION

Natural gases and liquefied petroleum gases are widely used as fuels for domestic, commercial and industrial purposes, e.g., for heating and/or cooking. As a result, there is often a danger that leakage of such gas from piping and other apparatus will contaminate the surrounding environment, creating a dangerous condition. For example, alkane gases such as methane are extremely combustible and furthermore could poison individuals if present at too great a level in enclosed surroundings. Moreover, small quantities of carbon monoxide can escape from such flowing gas streams into the environment, or could be generated by incomplete combustion of natural gas. Carbon monoxide is odorless and colorless, so that the contaminating levels are not readily observable by individuals. However, carbon monoxide is absorbed by an individual's lungs and reacts with the hemoglobin in the blood to form carboxyhemoglobin (COHb), reducing oxygen carrying capacity of the blood. Therefore, presence of carbon monoxide in an environment above certain levels is extremely dangerous and can easily poison individuals unaware of its presence.

Accordingly, there is a need to provide for suitable detection and concomitant alarm of unwanted fluid, i.e., gaseous contaminants in order to prevent unsafe or dangerous conditions from developing, e.g., in an enclosed environment. In this regard, various detectors for carbon monoxide and alkanes such as methane gas have been developed.

Various residential carbon monoxide gas detectors are found in the prior art and typically function to sound an audible alarm when a specified environmental CO concentration is detected. Carbon monoxide sensing elements employed within such detectors typically comprise a metal oxide layer on a ceramic substrate. When the ceramic substrate is heated to a high temperature, e.g., 200–400° C., the resistance of the metal oxide varies as a function of the environmental CO concentration. The sensing element can thus be employed as a variable resistor in a calibrated detection/alarm circuit which continuously monitors the environmental CO concentration and sounds an alarm upon the detection of hazardous levels.

Methane detectors which employ metal oxide semiconductor sensors are also in the prior art. As with CO sensors, many methane sensors also operate by maintaining the ceramic substrate at a high temperature such that the resistance of the metal oxide predictably changes as a function of ambient $CH_4$ concentration. Methane sensors are available which are relatively insensitive to the presence of carbon monoxide, and vice versa.

False alarms and/or gas detection inaccuracies due to the presence of airborne contaminants are often a problem with CO and $CH_4$ detectors. The sensing elements are typically sensitive to the presence of airborne gases and vapors such as alcohols, solvents and water vapor. In the common household environment, the use of cleaning agents, paints, turpentine, solvents, etc., produce vapors which can alter the resistance of the sensing element, thereby causing false alarms in the detection of the target gas.

When carbon monoxide enters a person's bloodstream, it reacts with hemoglobin (Hb) to form carboxyhemoglobin (COHb). A person is in danger of carbon monoxide poisoning when the person's COHb level exceeds a specific level, such as the levels promulgated by Underwriters Laboratories UL2034 carbon monoxide exposure specification. An individual's COHb level is a function of their exposure time to the environmental CO concentrations. False alarms are particularly a problem in prior art CO sensors because these sensors do not accurately model the COHb level that would be present in the exposed person's bloodstream. For example, a relatively high environmental CO concentration that is present for only a very short time duration often causes an alarm to be sounded in prior art CO sensors when such exposure would actually produce a COHb level well below the danger level.

U.S. Pat. No. 4,896,143 to Dolnick et al. discloses a CO sensor which is operatively connected to a microprocessor for calculating doses of carbon monoxide. The values of CO are accumulated over time, with the dose measurement being made by adding a measured value of CO concentration, which may be weighted, to a memory register each time the value is determined. An alarm is issued if the accumulated value reaches a predetermined value. A drawback of this technique is that the physiological response is not accurately modeled, which may lead to false alarms and/or under-detection of CO.

SUMMARY OF THE INVENTION

Accordingly, it is an object of the present invention to improve reliability in detection of combustible, toxic or noxious fluids such as carbon monoxide and methane.

It is a more particular object of the present invention to more accurately correlate sensing of toxic carbon monoxide gas in a closed environment with equilibrium levels existing in an individual's blood stream and adjusting alarm signals accordingly.

It is also an object of the present invention to improve selectivity for sensing certain gaseous contaminants and vapors as opposed to other gaseous contaminants and vapors.

It is a further object of the present invention to improve detection of dangerous threshold levels of fluid, i.e., gaseous concentration and at the same time minimize or eliminate unwanted generation of false alarms.

These and other objects are attained by the present invention which is directed to a gas detector comprising a carbon monoxide (CO) sensor for measuring an environmental CO concentration and providing a variable electrical output responsive thereto, plus a processor responsive to samples of the electrical output for computing a carboxyhemoglobin (COHb) level of an individual as if exposed to the measured CO concentration and providing an output signal based upon the COHb level computed. The present invention is also directed to a gas detector comprising a filter of hydrophobic zeolite disposed upon a transducer composed, e.g., of metal oxide such as stannous or stannic oxide. The hydrophobic zeolite acts to filter out interfering fluid, i.e., gaseous particles such as isopropanol, ethanol and other high molecular weight vapors which might set off false alarm readings if detected by the metal oxide transducer which can ideally detect presence of methane gas. In a preferred embodiment, sensors for methane and carbon monoxide are incorporated into a single device which can be positioned within an enclosure to accurately sense for presence of both these gases.

In an illustrative embodiment of the present invention, a gas detector is disclosed which includes a CO sensor and a processor. The CO sensor senses an environmental CO concentration and provides a variable electrical output in response. The processor receives digitized samples of the sensor's electrical output and computes, with each measurement sample, a COHb level of a hypothetical person exposed to the CO concentration sensed. The computation involves determining an equilibrium COHb level for each measurement sample, which is compared with a previously computed COHb level associated with previous measurement samples. The previously computed COHb level is updated based on the comparison. When the computed COHb level is above a predetermined danger threshold, the processor causes an audible alarm and visual indicator to be activated to alert any persons present.

The gas detector can further include a $CH_4$ sensor coupled to the processor for sensing $CH_4$ levels. The $CH_4$ sensor is insensitive to the presence of CO, and vice versa. An alarm is activated when the $CH_4$ levels detected are above a danger threshold. A hydrophobic zeolite filter is disposed on the $CH_4$ sensor to filter atmospheric gases and/or vapors such as alcohols and solvents from the sensing element and thereby prevent erroneous sensor readings. A similar zeolite filter can also be placed on the sensing element within the CO sensor to improve performance. When utilized in accordance with the present invention, the hydrophobic zeolite filter allows water vapor to pass therethrough. The adsorption sites on the filter are thereby not taken up with water molecules, so that the adsorption sites on the zeolite filter are available to adsorb the atmospheric gases/vapors described supra. Furthermore, even if water vapor has been adsorbed to a certain extent upon the hydrophobic zeolite filter, nevertheless contact with these other atmospheric constituents will displace the water molecules so that the filter is always available to adsorb such hydrocarbons over water.

BRIEF DESCRIPTION OF THE DRAWINGS

For a better understanding of the present invention, reference is made to exemplary embodiments thereof, considered in conjunction with the accompanying figures in which like reference numerals designate like elements or features, in which:

FIG. 4 illustrates a table of linear approximation functions for % COHb rate of increase;

DETAILED DESCRIPTION OF THE PREFERRED EMBODIMENTS

Figure 1:
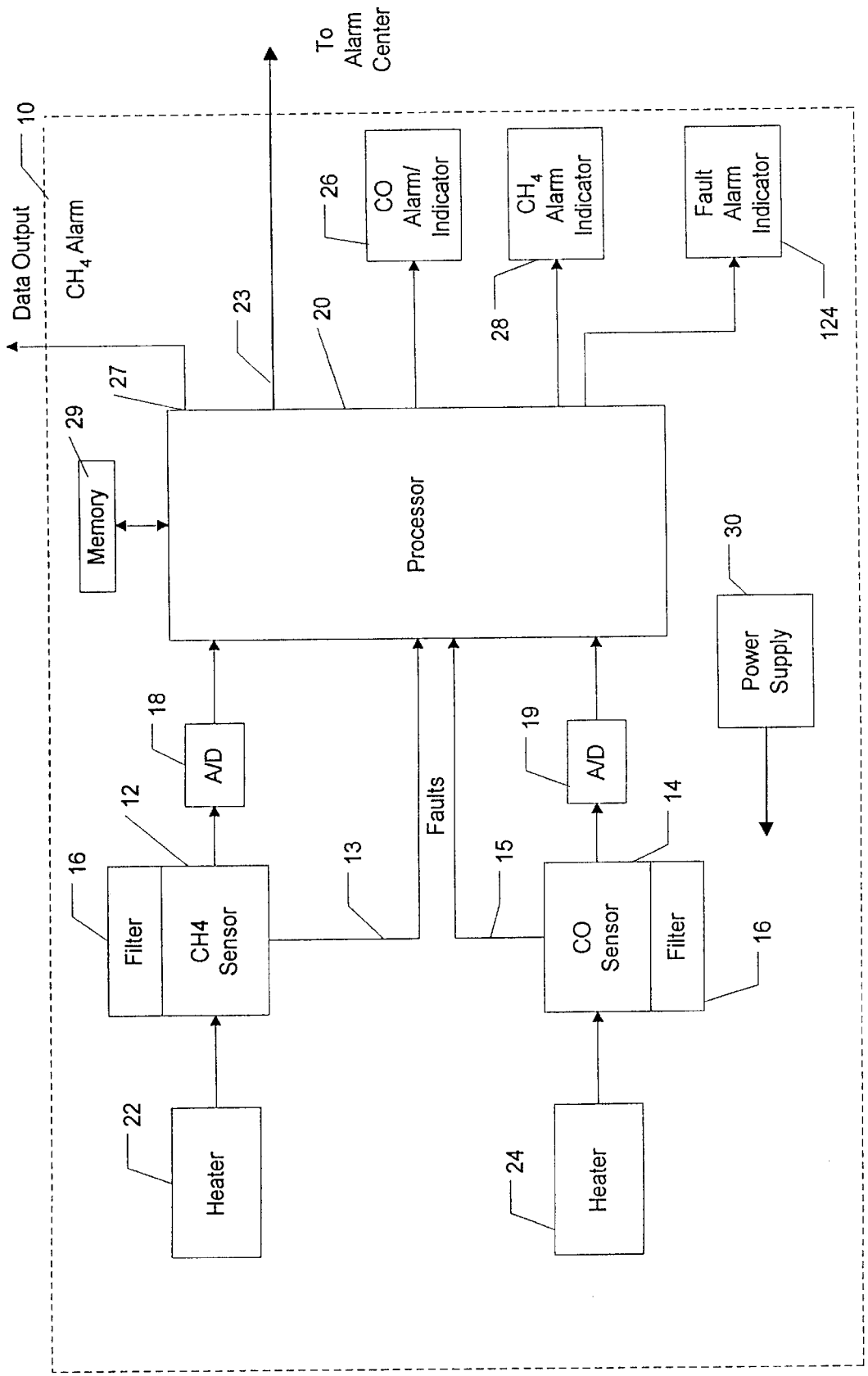
FIG. 1 is a schematic block diagram of a $CH_4$/CO alarm in accordance with the present invention.

Referring to FIG. 1, an illustrative embodiment of a carbon monoxide/methane alarm in accordance with the present invention is shown, designated generally as 10. Alarm 10 is particularly adapted for residential use and is preferably packaged for simple mounting on a wall or ceiling.

CO sensor 14 and $CH_4$ sensor 12 independently measure environmental CO and $CH_4$ concentrations respectively, in the vicinity of the alarm. The sensors each provide an analog voltage output indicative of the respective gas concentration measured. Each sensor 12 and 14 includes a sensing element that changes its electrical characteristics in response to the associated target gas (CO or $CH_4$) concentration, and electronic circuitry operatively coupled to the sensing element to provide the analog voltage output as a function of the target gas concentration. Preferably, the sensing elements are of the metal oxide/semiconductor type, e.g., tin oxide sensing element on a ceramic substrate. Such sensing elements are known in the art and are commercially available from various manufacturers. These sensing elements are operative to change their resistances in dependence on the incident CO or $CH_4$ gas. The $CH_4$ sensor element of sensor 12 is designed to be relatively insensitive to the presence of CO, and the CO sensing element of sensor 14 is relatively insensitive to the presence of $CH_4$. As such, each sensor output is substantially indicative of only the associated target gas $CH_4$ or CO it is designed to detect.

For proper operation of sensors 12 and 14, heaters 22 and 24 are respectively employed to heat the ceramic substrates of the sensing elements therein to a high temperature. Typically, this temperature is in the range of 300–500° C. and is maintained during operation of the alarm. The sensing elements respond properly to their target gases only at specific temperatures peculiar to the sensing element employed. Sensor element manufacturers typically specify recommended operating temperatures. The heaters 22 and 24 may include electronics to sense faults in the heaters, such as open circuited conditions. Logic level outputs indicative of heater faults are provided to processor 20, which responds by activating fault alarm/indicator 124 when faults are detected.

Electronic circuitry (not shown) within gas sensors 12 and 14 provide the analog output voltages as a function of the target gas concentration. Recommended electronics are typically specified by sensor element manufacturers and thus, are well recognized and available within the electronic circuitry art. Preferably, the sensor electronics include fault detection circuitry which provides logic level outputs on respective lines 13 and 15 indicative of sensor fault conditions such as an open circuited sensor. Processor 20 is responsive to these outputs and activates fault alarm/indicator 124 when appropriate.

A hydrophobic zeolite molecular sieve filter 16, 16' covers the sensing elements of each respective sensor 12 and 14. Filters 16, 16' function to filter out relatively large molecules such as alcohols while allowing the smaller molecules $CH_4$ and CO to pass. In the household environment, gases and vapors are commonly generated by paints, solvents, cleaners, liquid alcohol, and so forth. As a result, the sensitivity of each sensor to the associated target gas is unaffected or only minimally degraded by the presence of undesirable gases and vapors. Consequently, the occurrence of false alarms is reduced, as well as the interference with detection of dangerous levels of the target gas.

In particular, a hydrophobic zeolite molecular sieve filter is installed upon the sensor for methane gas, preferably over both respective sensors for methane and carbon monoxide gases. A description of zeolites can be found at Breck and Anderson, "Molecular Sieves", Kirk-Otluner Encyclopedia of Chemical Technology, Third Edition, Volume 15, John Wiley & Sons, Inc., New York (1981), pp. 638–669. More specifically, zeolites are constituted by hydrated silicates of aluminum and sodium, potassium, magnesium and/or calcium of the structural formula $M_{x/n}((AlO_2)_x(SiO_2)_y)wH_2O$ where M is a cation and n represents its valence, w represents the number of water molecules per cell, and x and y represents the total number of tetrahedra per unit cell.

Zeolites are especially suitable as molecular sieves, constituted by microporous structures composed of crystalline aluminosilicates. Such microporous structures present extremely small pore sizes, in the range of 5–10 Angstrom units. The aluminosilicates forming these sieves possess the ability to undergo dehydration with little or no change in crystalline structure. The thus-empty cavities in the microporous structure possess a strong tendency to adsorb other particulate structures which come into contact with it. As a result, a sieving action is generated which allows for separation of smaller and larger molecules, e.g., in a fluid. As such, zeolites are capable of being extremely effective in gas filtering and separation. Such molecular sieve-oriented zeolites possess the specific chemical formula of $$M_{2/n}O \cdot Al_2O_3 \cdot ySiO_2 \cdot wH_2O.$$

Molecular sieve zeolites can be naturally occurring or can be synthetically prepared. As noted supra, all zeolites have a high affinity for water and other polar molecules and can therefore be used, e.g., for drying gases and liquids. In the present invention, the zeolites are converted into hydrophobic form. For example, a synthetic zeolite such as synthetic mordenite can be dealuminated by acid treatment to increase the silicon/aluminum ratio. The $SiO_2/Al_2O_3$ ratio can be increased to about 100 (e.g., the range of about 90–100 and above), so that water-adsorbing capacity is essentially eliminated and the molecular sieve becomes hydrophobic. Therefore, when such hydrophobic zeolite is incorporated as a filter on the sensing device of the present invention, water is not adsorbed and passes therethrough while molecules such as isopropanol, ethanol and other high molecular weight vapors are prevented from passing through the filter, with the result that only smaller organic compounds, i.e., methane gas, can pass through the filter and therefore be detected by the sensor.

One benefit of utilizing a hydrophobic zeolite molecular sieve filter instead of activated carbon or other similar adsorbent media, is that hydrophobic zeolite does not adsorb water vapor so that adsorption capacity is not significantly reduced by water vapor adsorption. Molecular sieves such as activated carbon quickly lose their ability to filter when exposed to high relative humidity conditions. Additionally, the hydrophobic zeolite filter media can be effectively regenerated using simple resistive heaters which is not possible with activated carbon media.

The filters applied on the sensors in accordance with the present invention are developed from high silica molecular sieves, e.g., "high silica" zeolites and are therefore hydrophobic. Such filters exhibit a high selectivity for organic vapors, even under humid conditions. High silica zeolites possess crystalline, inorganic silica-alumina structures, in addition to being non-combustible and nonreacted to most airborne gases.

Especially preferred high silica molecular sieve for use with the present invention are marketed under the trade names HiSiv 1000 and HiSiv 3000 by UOP Molecular Sieves, DesPlains, Ill. HiSiv 1000 and HiSiv 3000 are high silica zeolites possessing pore structure for adsorbing molecules with critical diameters up to 0.8 and 0.6 nanometers, respectively. These molecular sieves are especially suitable for adsorbing relatively small molecules and low-boiling solvents such as alcohols, aldehydes, ketones, esters, aliphatics, aromatics and chlorinated hydrocarbons. In particular, HiSiv 1000 and HiSiv 3000 adsorb vapors from ethanol, acetone and methylene chloride extremely well, so that such vapors will not contact the sensors and activate the same to generate false alarms. Therefore, the zeolites effectively filter out all vapors except extremely small molecular vapors such as CO, $CH_4$ and water. Accordingly, these molecular sieve zeolites perform excellently as filtering mechanisms upon CO and $CH_4$ detectors in accordance with the present invention.

The particular HiSiv products are available in powder form, with particle sizes of less than 200 mesh. Additionally, these products are also both available in the shape of approximately 1.5 mm. pellets in size, and Tri-Lobe 3 mm or 6 mm pellets under the trade name TriSiv by UOP. The product HiSiv 1000 possesses an average pore size of about 8 Angstrom units while the product HiSiv 3000 possesses an average pore size of 6 Angstrom units. HiSiv 3000 is especially suited for adsorbing small molecules and low-boiling solvents such as ethanol, acetone and methylene chloride while HiSiv 1000 is especially suited for adsorbing larger molecules 0.6–0.8 nanometers in size, e.g., higher boiling solvents such as toluene and methyl isobutyl ketone. In a preferred embodiment of the methane sensor in accordance with the present invention, a blend of these two products is provided, with about 25% HiSiv 1000 and about 75% HiSiv 3000 being blended together to provide the appropriate size filter.

Any conventionally-available gas detection sensor, e.g., for low molecular weight alkanes or carbon monoxide, can be provided with a hydrophobic zeolite molecular sieve in accordance with the present invention to improve detection of the requisite gaseous contaminants. One such sensor is marketed by Figaro USA, Inc., Wilmette, Ill. under the name Figaro Gas Sensor TGS 813/813C. This sensor possesses excellent sensitivity to low molecular weight alkanes, e.g., methane, propane and butane, making this an excellent sensor for domestic gas leak detection. At the same time, this sensor exhibits very high sensitivity to "noise gases"; incorporating the hydrophobic zeolite molecular sieve supra reduces occurrence of false or nuisance alarming. The TGS 813 sensor comprises a sintered bulk semiconductor composed principally of tin dioxide ($SnO_2$) and situated on a ceramic tube together with electrodes therefor. A heater coil, composed of 60 micron diameter core possessing a resistance of 30 ohms, is situated within the ceramic tube. A stabilized 5 volt heater supply provides current to the heating coil while a circuit voltage not exceeding 24 volts is supplied to the tin dioxide semiconductor itself. Operation and calibration of the Figaro Gas Sensor TGS 813/813C is described in a specification brochure published by Figaro USA, Inc.

Basically, the resistance of the tin dioxide semiconductor itself drops when contacted by a target gas, e.g., methane. As the concentration of gas increases, the resistance of the tin dioxide semiconductor drops, with concomitant flow of current therethrough increasing. Eventually, the current flow will increase to an alarm level and thereby activate an appropriate alarm coupled into the sensor circuit, e.g. a buzzer.

A sensor especially suited for carbon monoxide gas detection is manufactured under the trade name "G" Series by Capteur Sensors & Analysers Limited, Abingdon Oxon, England. These sensors are also composed of a metal oxide sensing element and are provided in a casing with a resistor circuit in similar fashion to the methane gas sensor described supra. In particular, different levels of heater resistance and sensor resistance are provided so that the CO sensor does not respond to methane and hydrogen. For example, the sensor is heated to a temperature of about 390° C. by the heater which possesses a resistance of about 15 ohms at this temperature. The sensor itself possesses a resistance of about 52 kilo-ohms at this temperature, this resistance increasing as the concentration of CO increases.

More particularly, the sensor resistance under exposure to 100 ppm. CO concentration rises to 86 kilo-ohms, and to 105 kilo-ohms under 200 ppm. CO concentration. The current flow through the CO sensor will concomitantly drop and thereby a voltage representing ambient CO concentration will be generated. Additionally, the sensing element can be covered with a carbon filter to block out all vapor penetration except for carbon monoxide. Operation and calibration of the "G" series carbon monoxide sensors is described in a specification brochure published by Capteur Sensors & Analysers Limited.

Figure 7:
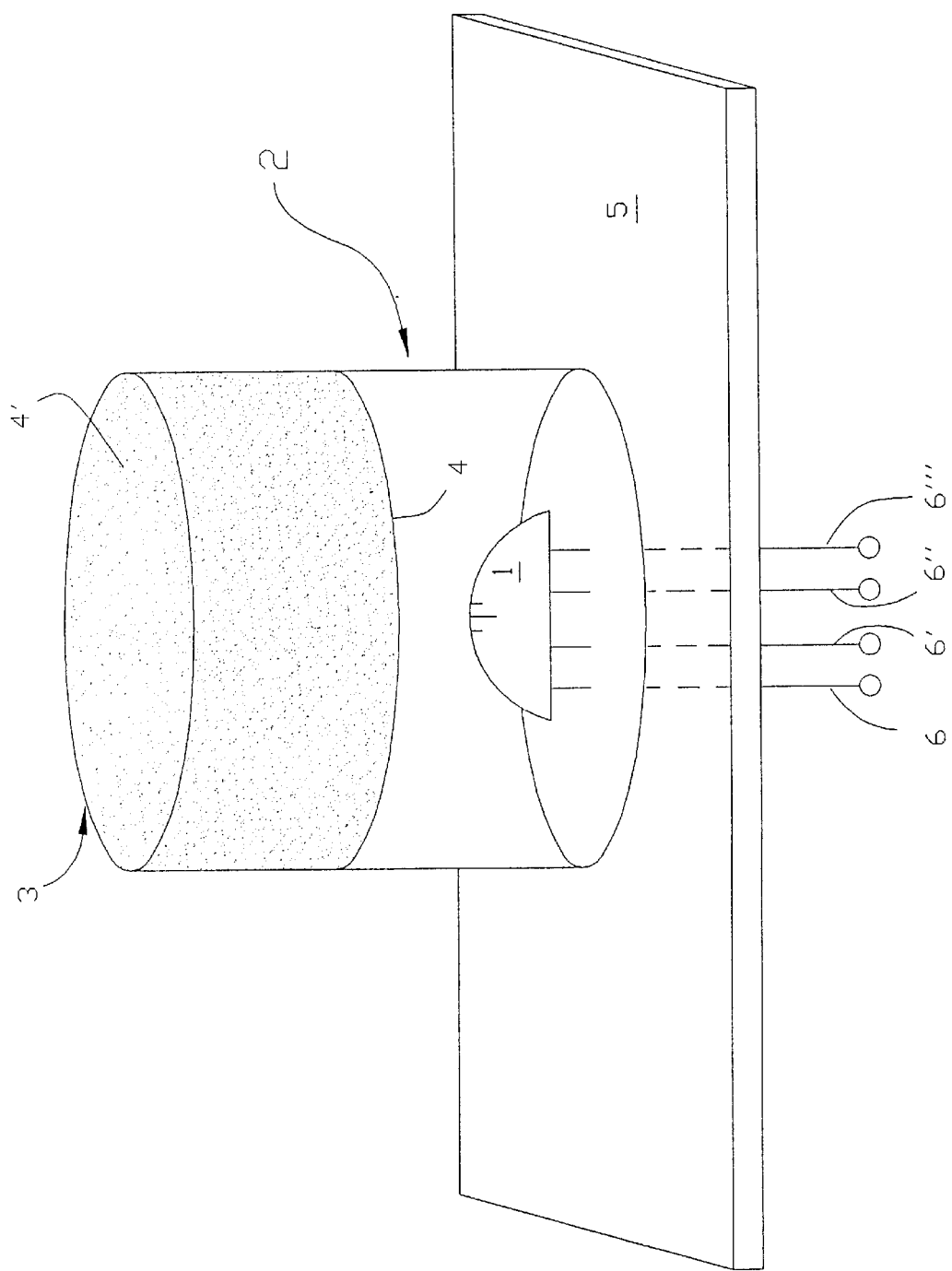
FIG. 7 illustrates an exemplary zeolite filter disposed in relation to a gas sensor in accordance with the present invention.
Figure 8:
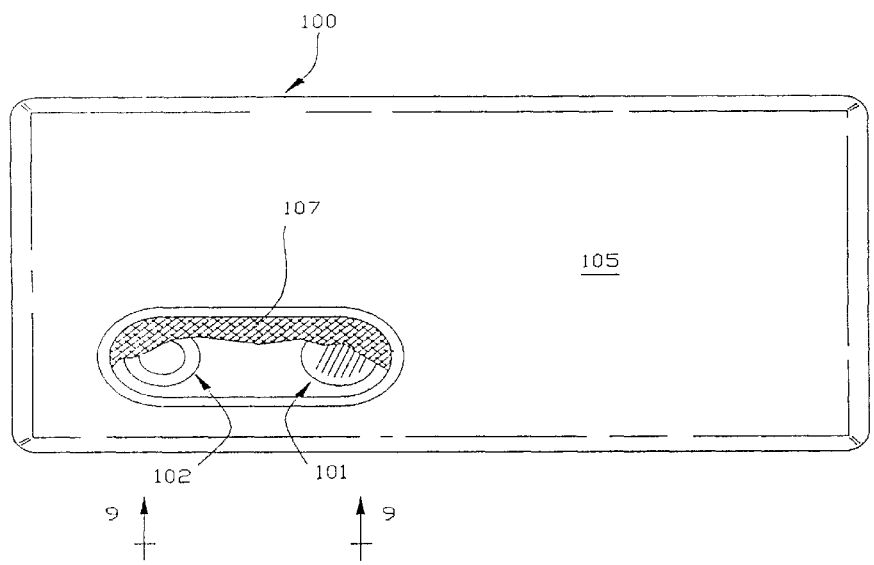
FIG. 8 is a top view, partially broken away, and illustrating a zeolite filter disposed in relation to a composite $CH_4$ and CO sensor in accordance with the present invention.
Figure 9:
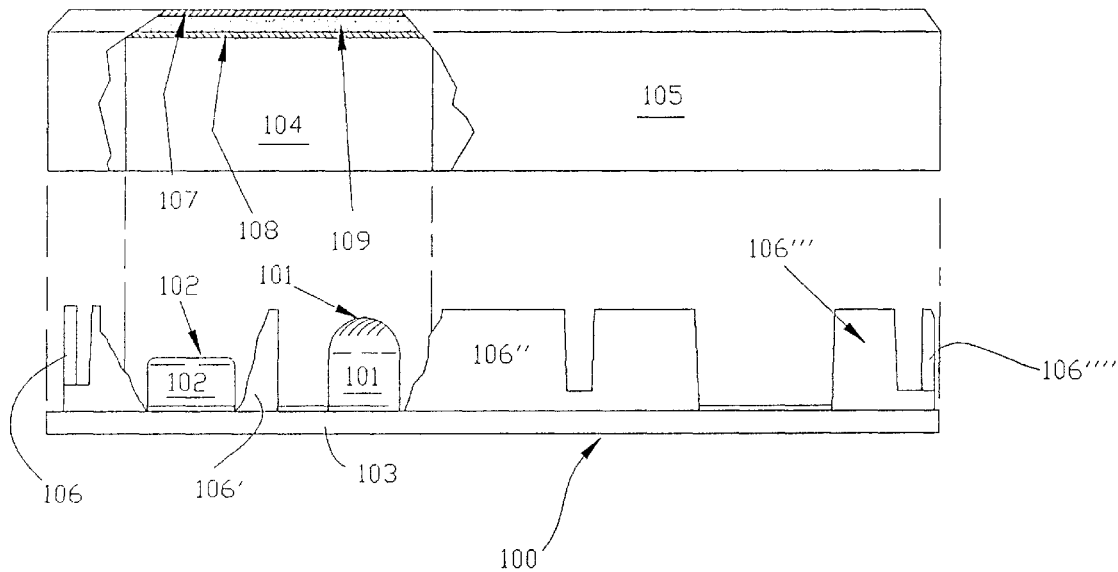
FIG. 9 is an exploded side elevational view, partially in section, of the composite sensor of FIG. 8 in the direction of arrows 9—9.

The two sensors can be separately incorporated into the invention system as illustrated in FIG. 7 or combined into a composite sensor unit as illustrated in FIGS. 8 and 9. More particularly, FIG. 7 illustrates a single gas sensor 1 disposed within a casing 2 that contains a zeolite filter or sieve 3 mounted a distance away from the sensor 1. The zeolite filter or sieve 3 is retained in position between two screens 4, 4' composed, e.g., of stainless steel. The casing 2 itself can be composed of any suitable material, e.g., molded plastic, and can be substantially cylindrical in shape as illustrated. The entire sensing unit can be mounted upon a suitable support 5 as illustrated, which can, in turn, be mounted upon a ceiling or wall panel. In this regard, the sensor 1 comprises four leads 6, 6', 6" and 6'" which pass through the casing 2 and support 5 and are connected to appropriate terminals.

Sensor 1 illustrated in FIG. 7 is a carbon monoxide sensor of the type, e.g., manufactured by Capteur Sensors & Analysers as described supra. In this regard, two of the four leads 6, 6', 6" and 6'" illustrated in FIG. 7 are coupled to form a sensor resistance circuit while the other two leads are coupled to form a heat resistance circuit, i.e., to heat the sensor 1 as described. The zeolite filter 3 positioned as shown in FIG. 7, operates to effectively filter out all vapors except extremely small molecular vapors such as CO, $CH_4$ and water. While a CO sensor has been illustrated in FIG. 7, it is noted that a methane sensor, manufactured by Figaro U.S.A. as described supra, can be substituted in place of the CO sensor and function equally well to detect the presence of methane gas.

Furthermore, methane gas and carbon monoxide sensors can be combined into a single sensing unit 100 (FIGS. 8 and 9). More particularly, carbon monoxide sensor 101 and methane sensor 102 are each mounted upon a support base 103 in turn mounted upon a support such as a ceiling or wall panel. Each sensor 101 and 102 is provided with appropriate electronic circuitry (not illustrated) as described supra. Casing 104 is designed to fit over both sensors 101 and 102 in similar fashion to the casing 2 shown in FIG. 7, when the cover member 105 is lowered and secured upon support base 103 from the raised position shown in FIG. 9. Raised wall members 106, 106', 106", 106'" and 106"" are arranged to securely mate with an inner surface of cover member 105 when the cover member 105 is lowered upon the support base 103.

Casing 104 is mounted upon an upper inner surface of cover member 105 as illustrated in FIG. 9. More particularly, two screens 107 and 108 are provided as shown in FIG. 9, between which hydrophobic zeolite filter 109 is retained. Appropriate filtering of all undesired or "non-target" gases by the zeolite filter 109 in relation to both the carbon monoxide 101 and methane 102 sensors is effectively provided so that it is now possible to effectively combine said sensors 101 and 102 in a single gas sensing unit 100 which can be conveniently mounted at any required location within an environment to accurately and swiftly detect presence of methane or carbon monoxide. It is no longer necessary to separately arrange, mount and couple carbon monoxide and methane sensors from one another. Additionally, the support base 103 and cover 105 can be each composed of the same material as casing 104, namely injected molded plastic. In particular, support base 103 is composed of plastic backing upon a base.

Operation of the invention system for monitoring carbon monoxide gas detection will now be described with reference to FIGS. 1–6.

The analog output voltages of sensors 12 and 14 are sampled and digitized by analog to digital (A/D) converters 18 and 19 respectively, with a typical sampling rate in the range of 1 to 5 seconds, for example. The digitized outputs are provided to processor 20 which has a software program stored therein to determine whether dangerous levels of either $CH_4$ or CO have been detected. A memory 29 stores data used within calculations by the processor. Processor 20, memory 29 and A/D converters 18 and 19 can be incorporated within a microcontroller or Application Specific Integrated Circuit (ASIC).

If hazardous levels of either CO or $CH_4$ gas are detected, processor 20 provides a specific logic level output to CO alarm/indicator 26 or $CH_4$ alarm/indicator 28, or both, as the case may be, to activate the respective alarms and visual indicators. Alarm/indicators 124, 26 and 28 may have a common audio alarm element with separate light emitting diode (LED) indicators to indicate which hazardous condition or fault is present. Electronics are included therein to drive the alarm element and indicators responsive to the logic level outputs provided by the processor. A power supply 30 is employed to power the alarm as well as the other electronic components within the overall $CH_4$/CO alarm 10.

Optionally, the $CH_4$/CO alarm 10 can be linked via line 23 to a centralized alarm center such as a fire station. When dangerous gas levels are detected, the alarm center would be alerted. The link to the alarm center could be a wireline or wireless communication link. Memory 29 would store an identification code identifying the location that is being monitored by the alarm. When danger levels are detected, processor 20 would transmit the ID code to the alarm center along with information pertaining to the gas levels detected. Personnel at the alarm center would be equipped to quickly respond to the emergency situation.

The memory 29 could also be used to store measured CO and $CH_4$ concentration data in a log for subsequent retrieval. Computed COHb data can also be stored in a log, as will be described infra. An external computer would retrieve the log data via appropriate connection to I/O port 27 along with suitable commands.

Processor 20 determines whether a hazardous methane condition exists by comparing the measured $CH_4$ concentration to a predetermined threshold level, e.g., 3,000 ppm., stored within memory 29. Once the threshold is met or exceeded, the $CH_4$ alarm is sounded.

The processor determines whether a hazardous environmental CO concentration exists by computing a carboxyhemoglobin (COHb) level that would exist in a person exposed to the CO concentration. The COHb level that would exist is a function of the environmental CO concentration and the exposure time to that CO concentration, as well as the COHb level, if any, that existed previously. COHb danger levels are promulgated by Underwriters Laboratories specification UL 2034. Once processor 20 determines that a predetermined COHb danger level COHb$_{DL}$ is reached or exceeded, e.g., a 10% COHb level, processor 20 activates CO alarm 26. Processor 20 also automatically activates CO alarm 26 even if COHb$_{DL}$ is not yet reached whenever very high concentrations of CO$_{ppm}$ are detected, e.g., 800 ppm or above.

Figure 2:
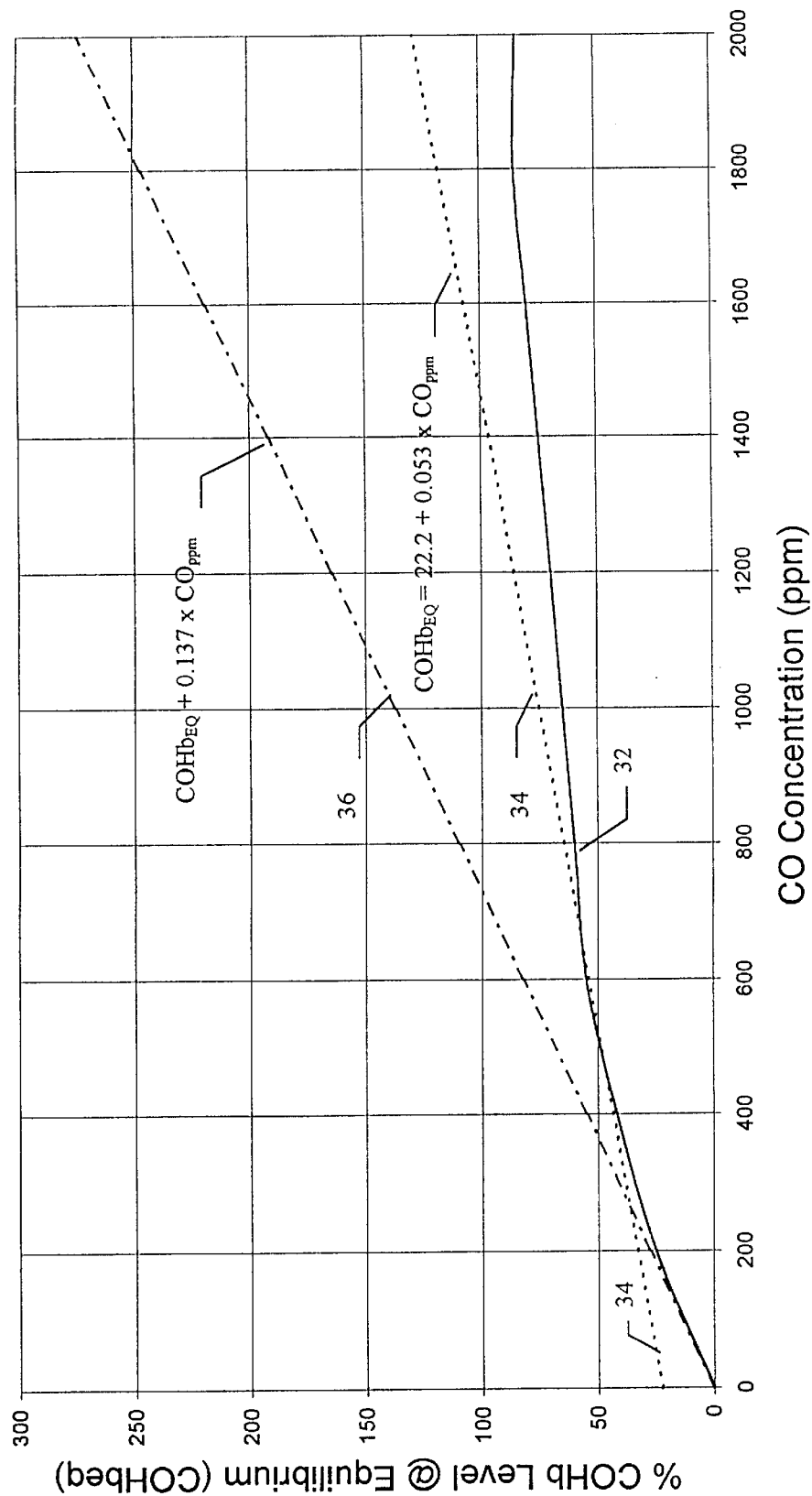
FIG. 2 is a graph of COHb equilibrium level vs. environmental CO concentration.

The blood's COHb level, represented by the percentage of COHb relative to all hemoglobin in the bloodstream, increases as a function of environmental CO concentration and exposure time. Hereafter, the environmental CO concentration in parts per million (ppm) will be referred to as CO$_{PPM}$. For any value of CO$_{PPM}$ that a person is exposed to, there is an equilibrium COHb level COHb$_{EQ}$ that will be eventually be reached with time. In FIG. 2, curve 32 represents % COHb level at equilibrium (COHb$_{EQ}$) vs. environmental CO concentration (CO$_{PPM}$) for an average person found in the text entitled "Medical Toxicology: Diagnosis and Treatment of Human Poisoning" by Ellenhorn and Barceloux and published in 1988 by Elsevier Science Publishing Company, Inc., New York, N.Y. This curve can be linearly approximated by the following equations (1) and (2):

$$COHb_{EQ} = 0.137 \times CO_{PPM}, \text{ for } CO_{PPM} < \sim 264 \text{ ppm} \quad (1),$$

$$COHb_{EQ} = 22.2 + 0.053 \times CO_{PPM}, \ 264 \text{ ppm} < CO_{PPM} < 800 \text{ ppm} \quad (2).$$

The dotted lines 36 and 34 of FIG. 2 are graphical representations of equations (1) and (2), respectively. It is understood that other linear or nonlinear approximations for curve 32 may alternatively be made.

Figure 3:
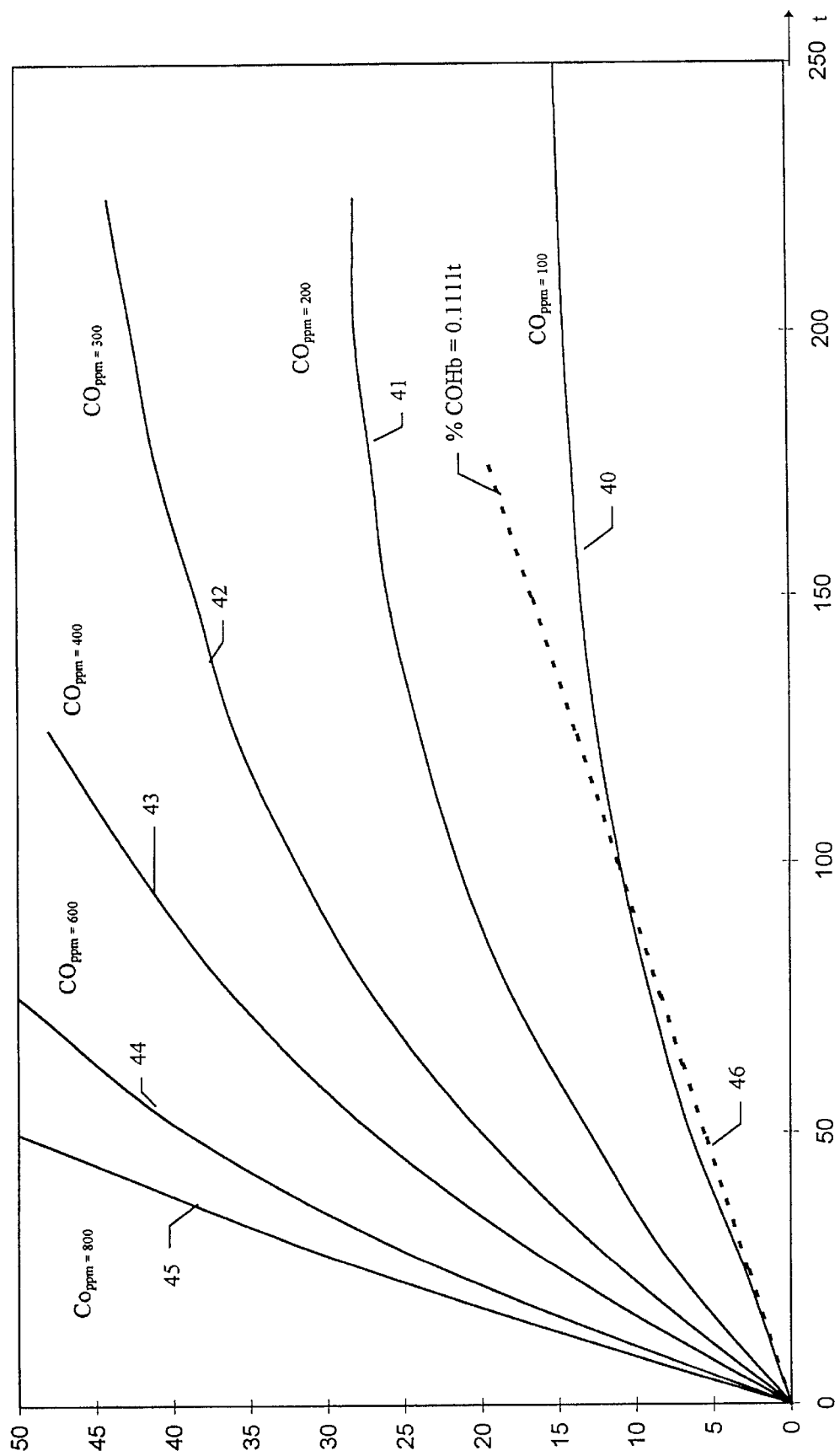
FIG. 3 illustrates curves of COHb levels as a function of exposure time for various environmental CO concentrations.

Referring to FIG. 3, % COHb level is shown plotted as a function of exposure time of an average person for various CO$_{PPM}$ concentrations. Curves 40–43 show % COHb vs. exposure time for CO$_{PPM}$ ranging from 100 to 400 ppm in increments of 100 ppm; curves 44 and 45 show the same for CO$_{PPM}$ equal to 600 and 800 ppm, respectively. The curves are based on data published in Underwriters Laboratory specification UL2034. For each curve, it is assumed that the person had a COHb level of zero percent in his or her bloodstream prior to being exposed to the respective CO concentration.

Each curve 40–45 can be approximated by a straight line for relatively low values of % COHb. For example, dotted line 46 is a linear approximation for curve 40 and is a plot of the function $$\% COHb = 0.1111t, \quad (3)$$

where t is exposure time.

Figure 5:
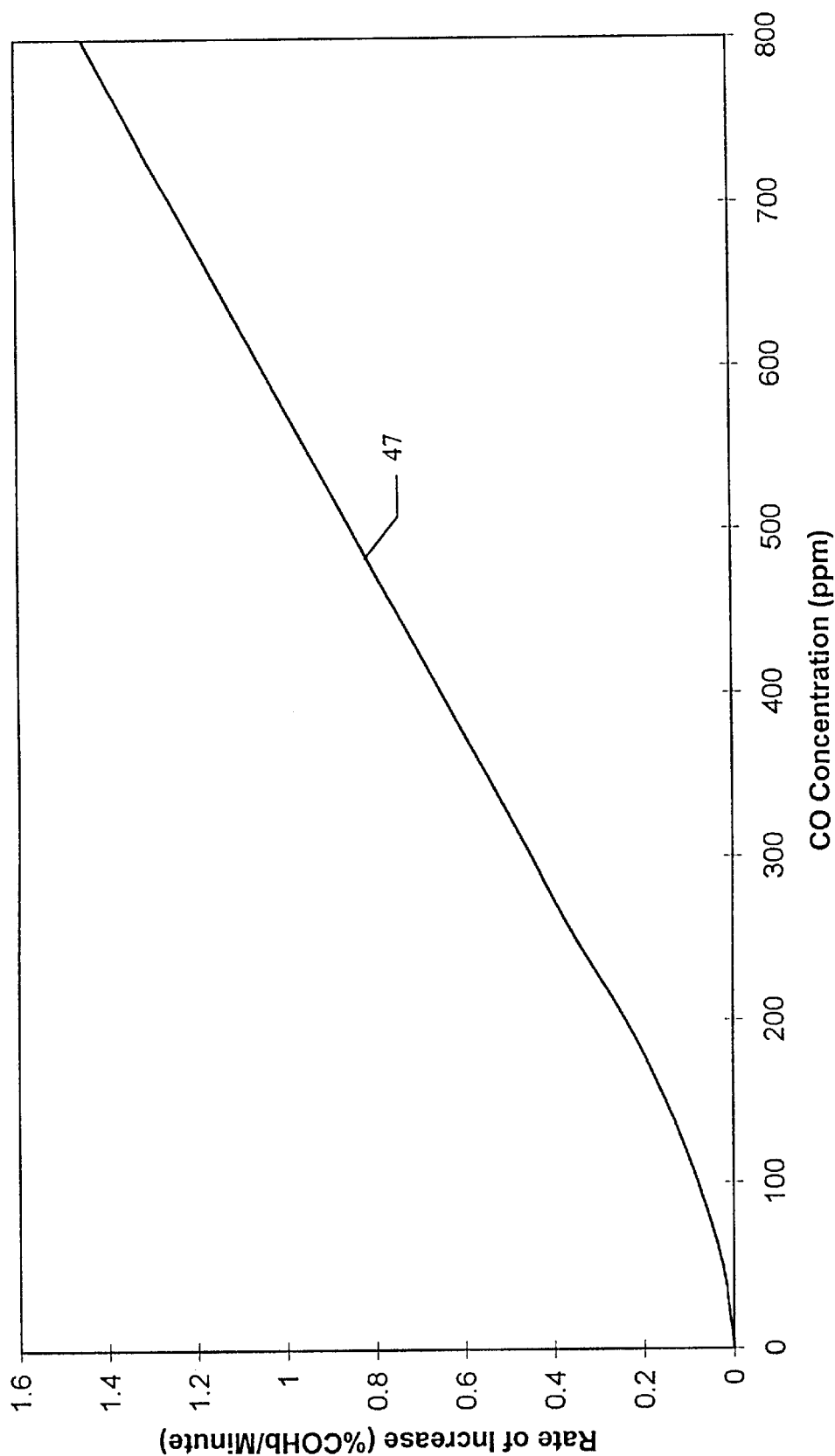
FIG. 5 is a graph of the rate of COHb increase versus environmental CO concentration based on a linear approximation.

As shown in the table of FIG. 4, each of curves 40–45 can be represented by a different linear function. From these linear functions, a plot of the rate of COHb increase as a function of environmental CO concentration (CO$_{PPM}$) can be constructed, as shown in FIG. 5. Curve 47 represents an approximated rate of COHb increase in % COHb/minute as a function of CO$_{PPM}$, for an average person, and for relatively low values of % COHb, e.g., below 10%.

Curve 47 may be approximated by a piece-wise linear approximation as follows:

Rate of COHb Increase (% COHb/minute)=0.000833×CO$_{PPM}$,

0<CO$_{PPM}$<54.1, 0.00151×CO$_{PPM}$−0.0366, 54.1<CO$_{PPM}$<138.2, and 0.00190× CO$_{PPM}$−0.0905,CO$_{PPM}$>138.2 \quad (4).

Figure 6:
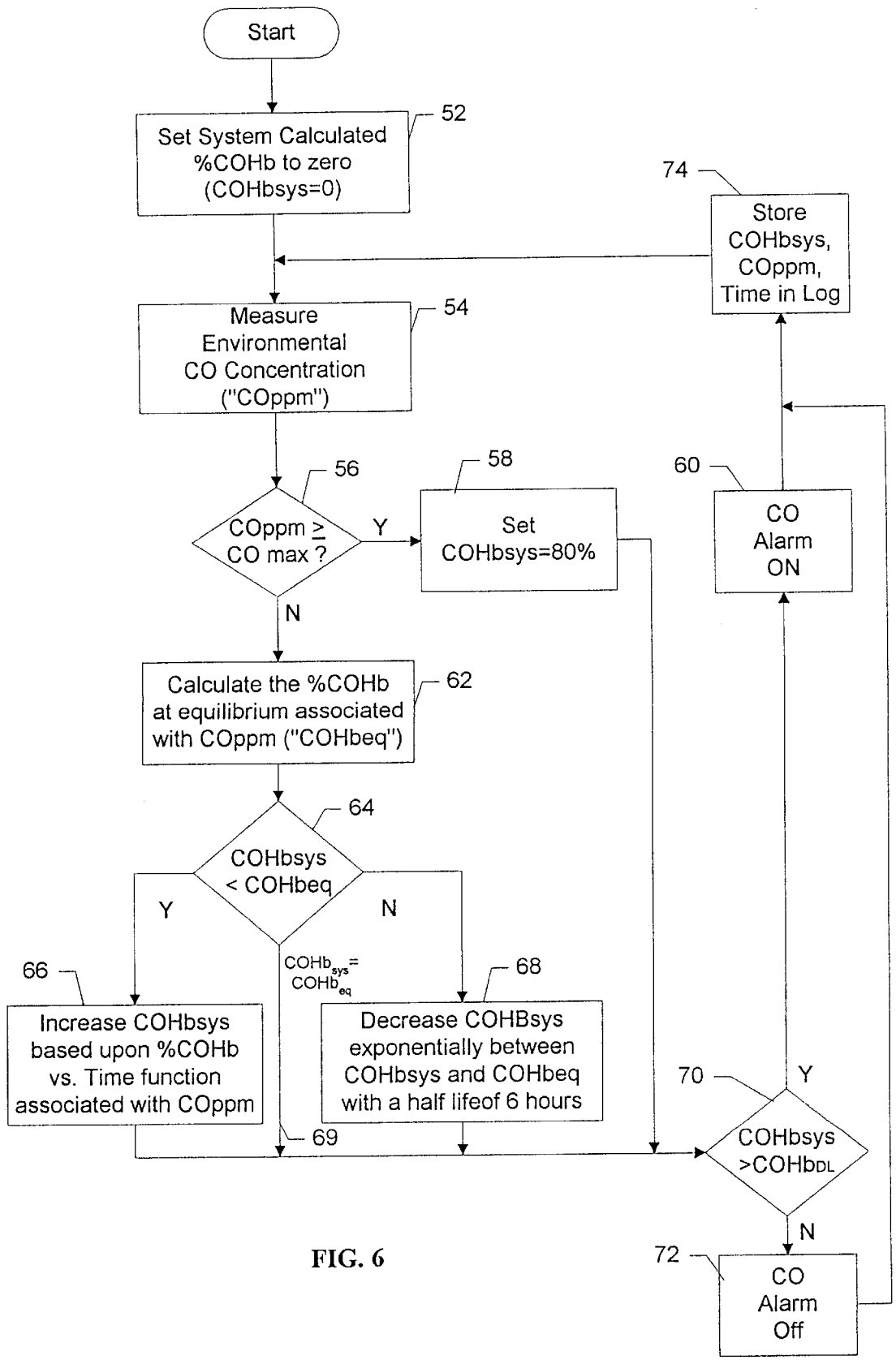
FIG. 6 is a flow diagram illustrating software steps in determining COHb levels.

FIG. 6 is a flow chart illustrating software routine steps running on processor 20 to determine COHb levels from the measured environmental CO concentration CO$_{PPM}$. When the CH$_4$/CO alarm 10 is first turned on, a "system calculated" % COHb level, designated as COHb$_{SYS}$, is set to a predetermined minimum level, e.g., zero percent. (Step 52). Next, the environmental CO concentration CO$_{PPM}$ is measured in step 54. As explained above in reference to FIG. 1, processor 20 receives digitized samples of CO$_{PPM}$ from A/D converter 19. The samples may be received periodically at a sampling rate on the order of 1–5 seconds. Each sample represents a new CO$_{PPM}$ measurement. In step 56, the CO measurement sample is compared to a predefined maximum CO level CO$_{MAX}$, e.g., 800 ppm. If CO$_{PPM}$ equals or exceeds CO$_{MAX}$, then COHb$_{SYS}$ is set to 80% in step 58, compared to COHb$_{DL}$ in step 70, and the CO alarm is automatically turned on in step 60. The 80% level represents a safe value at which to set COHb$_{SYS}$ when CO$_{ppm}$ is above full scale of the A/D converter 19. Notwithstanding the alarm activation, steps 54 and 56 are repeated. Hence, if the CO$_{PPM}$ level drops, the alarm may eventually be turned off, as will become apparent below.

If in step 56, CO$_{PPM}$ is less than CO$_{MAX}$, the % COHb at equilibrium (COHb$_{EQ}$) associated with the measured CO$_{PPM}$ is determined in step 62. This determination is based upon the values corresponding to curve 32 of FIG. 2. Thus, COHb$_{EQ}$ can be obtained either from a ROM look up table within the memory, or from an algorithm such as a linear algorithm based on equations (1) and (2) supra. In any case, COHb$_{SYS}$ is then compared to COHb$_{EQ}$ in step 64. If COHb$_{SYS}$ is less than COHb$_{EQ}$, then COHb$_{SYS}$ is increased in step 66 by an amount which is based upon the % COHb vs. exposure time function associated with CO$_{PPM}$ (FIG. 3). For example, the graph of FIG. 5, which is derived from the curves of FIG. 3, may be stored in another ROM look up table within the processor, such that an approximate rate of % COHb increase can be readily retrieved. A linear or nonlinear algorithm that approximates the curve of FIG. 5 could also be used to compute the rate of increase. A new value for COHb$_{SYS}$ is then obtained as follows:

$$COHb_{SYS} \text{(new)} = COHb_{SYS} \text{(old)} + \text{(rate of increase)} \times \text{(sampling interval)}, \quad (5)$$

where COHb$_{SYS}$ (old) is the value of COHb$_{SYS}$ prior to the update in step 66.

If in step 64, COHb$_{SYS}$ is greater than COHb$_{EQ}$, then COHb$_{SYS}$ is decreased exponentially between COHb$_{SYS}$ and COHb$_{EQ}$, (step 68) using a half life of about six hours, for example. The exponential decrease is based on the following equation:

$$COHb_{SYS}(\text{new}) = (COHb_{SYS}(\text{old}) - COHb_{EQ}) \times e^{-\frac{(\ln 2)(\Delta t)}{Y}} + COHb_{EQ}, \quad (6)$$

where COHb$_{SYS}$ (old) and COHb$_{SYS}$ (new) are the values for COHb$_{SYS}$ prior to and after step 68, respectively; COHb$_{EQ}$ was determined in step 62; $\Delta t$ is the sampling interval (in minutes); and Y is the half life for elimination of CO in minutes. It has been found through experimentation that a half life of six hours (360 minutes) is preferable, since this approximates the decay in the COHb level of an average person when environmental CO$_{PPM}$ concentrations drop. It is understood, however, that other values can alternatively be used for the half life. For example, if an additional safety factor is desired in the alarm, a longer half life would be selected.

With continuing reference to FIG. 6, once an updated value of $COHb_{SYS}$ is obtained in steps 66 or 68, the updated value is compared in step 70 to the COHb danger level $COHb_{DL}$, e.g., 10%. If in step 64, $COHb_{SYS}$ equals $COHb_{EQ}$, steps 66 and 68 are bypassed, as indicated by flow line 69, and step 70 is proceeded to directly. If the danger level is exceeded, the processor will command the CO alarm and indicator to be turned on in step 60 by supplying the appropriate logic level output thereto. If $COHb_{SYS}$ is below the danger level, the processor will supply the opposite logic level to the CO alarm and it will remain off in step 72. In any case, the updated value for $COHb_{SYS}$ is stored in the memory and replaces the previous value, and a new measurement is taken in step 54, whereupon the process is repeated.

The values computed for $COHb_{sys}$, as well as the measured $CO_{PPM}$ values and a time reference, can be stored in step 74 as a log in the memory 29 (FIG. 1) to record the levels over a length of time. The stored values can be subsequently retrieved by appropriate connection of an external computer to the processor. The log period could be on the order of days or weeks, depending on the storage capacity of the memory and on the sample time between stored data. When the storage capacity is reached, the processor would typically purge the memory of the oldest data. The external computer, when connected, could similarly purge portions of the memory by appropriate commands. It is noted that the measured methane levels could also be stored in a log for retrieval by the external computer at such time.

The following example is presented to illustrate the computation for the system calculated COHb level, $COHb_{sys}$, in a varying $CO_{PPM}$ environment. At the start, it is assumed that the environmental CO concentration $CO_{PPM}$ has been zero for a long period of time so that the subject's COHb level is zero. $CO_{PPM}$ then instantly becomes 200 ppm for one hour. At the end of the hour $CO_{PPM}$ becomes and remains 50 ppm.

EXAMPLES OF OPERATION

For the first hour, the human subject's COHb level will increase along the $CO_{PPM}$=200 ppm function of FIG. 3 (curve 41). This function intersects the 10% COHb level after 35 minutes have elapsed. At the end of the hour, the subject's COHb level is at 15.3%. At this point, $CO_{PPM}$ becomes 50 ppm and the subject's COHb level decreases exponentially with a six hour half life from 15.3% towards 8.2%, which is the COHb equilibrium value $COHb_{EQ}$ associated with a $CO_{PPM}$ of 50 ppm. (The 8.2% level can be interpolated from the curves of FIG. 2). After 50 minutes of this exposure, the subject's COHb level decreases to 14.7% and after 6 hours it becomes 11.75% (half way between 15.3% and 8.2%).

The accuracy in the computation of $COHb_{SYS}$ by the $CH_4$/CO alarm depends on the approximations used for the curves of FIGS. 2 and 3. For example, if linear functions are used to approximate curves 32 and 47, then in the example just presented, $COHb_{SYS}$ would reach 10% in about 34.5 minutes and will be about 17.4% at the end of one hour. $COHb_{SYS}$ would then decrease exponentially with a 6 hour half life from 17.4% towards 6.9%. After 50 minutes of exposure at 50 ppm, $COHb_{SYS}$ decreases to 16.4% and after 6 additional hours becomes 12.15% (half way between 17.4% and 6.9%). It should be noted that $COHb_{SYS}$ accuracy superior to that achieved by the linear approximation can be realized with closer analytical modeling of the above-mentioned exposure curves, whether via nonlinear algorithms or by means of look up tables corresponding to the curves of FIGS. 2 and 3. A small microcontroller of e.g., eight bits, can accomplish all these calculations.

It is to be understood that the embodiments described herein are merely exemplary and that one skilled in the art can make many modifications and variations to the disclosed embodiments without departing from the spirit and scope of the invention. All such variations and modifications are intended to be included within the scope of the invention as defined by the appended claims.

What is claimed is:

1. A gas detector, comprising
   a carbon monoxide (CO) sensor for measuring a CO concentration and providing a variable electrical output signal responsive thereto;
   a processor responsive to samples of said electrical output signal for computing a carboxyhemoglobin (COHb) level corresponding to the CO concentration such that when a present computed COHb level is less than a previous computed COHb level, a new present COHb level is computed based on a calculated exponential decay between the previous computed COHb level and the present computed COHb level.

2. The gas detector as recited in claim 1, further comprising a methane sensor for independently measuring a methane concentration independent of said CO sensor and providing a further electrical signal responsive to said measured methane concentration, the processor being responsive to the further electrical signal by activating a warning device whenever the methane concentration exceeds a predetermined threshold.

3. The gas detector as recited in claim 2, wherein the methane sensor includes a methane sensing element on a ceramic substrate, the gas detector further comprising a hydrophobic zeolite filter disposed in relation to the methane sensing element to filter other atmospheric gases.

4. The gas detector as recited in claim 1, wherein the CO sensor includes a CO sensing element on a ceramic substrate, the gas detector further comprising a hydrophobic zeolite filter disposed in relation to the CO sensing element to filter other atmospheric gases.

5. The gas detector as recited in claim 1, further comprises a memory for storing computed COHb levels for subsequent retrieval.

6. The gas detector as recited in claim 1, wherein the previous computed COHb level is zero at turn-on of the gas detector.

7. The gas detector as recited in claim 1, wherein the exponential decay is calculated based on a half life of absorbed CO elimination by an individual.

8. The gas detector as recited in claim 7, wherein the half life is about six hours.

9. The gas detector as recited in claim 1, wherein the calculated exponential decay is calculated by the formula:
   (new present COHb level)=present computed COHb level)+(previous computed COHb level-present computed COHb level)×exp $\{[-\ln(2)(\Delta t)]/Y\}$ where $\Delta t$ is a sampling time interval in minutes and Y is a half life of CO elimination.

10. The gas detector as recited in claim 1, wherein the variable electrical output signal comprises a variable output voltage, and further comprising an A/D converter for digitizing the output voltage to provide measurement samples to the processor.

11. The gas detector as recited in claim 1, further comprising a warning device responsive to the output signal provided by said processor, the warning device being activated when the computed COHb level exceeds a predetermined value.

12. The gas detector as recited in claim 1, further comprising a warning device responsive to the output signal provided by said processor, the warning device being activated when the CO concentration exceeds a specified maximum value.

13. A method for monitoring carbon monoxide (CO) concentrations and indicating a level thereof, comprising the steps of:

periodically measuring environmental CO concentration in an area;

determining a carboxyhemoglobin (COHb) equilibrium level corresponding to the measured CO concentration and an individual's physiology;

computing a COHb level of the individual as if exposed to the environmental CO concentration based on a relationship between a previously computed COHb level and the COHb equilibrium level;

providing an output signal based on the COHb level computed; and providing a warning signal based on the output signal to indicate if CO concentration exceeds a predetermined concentration, wherein the step of computing a COHb level includes:
increasing or exponentially decreasing a previously computed COHb level associated with previously measured samples when the equilibrium COHb level corresponding to the present sample is higher than or less than the previously computed COHb level, respectively, the increasing being based on a rate of COHb level increase associated with the environmental CO concentration of a present measurement sample, the exponentially decreasing being based on an exponential decrease in COHb level from the previously computed COHb levels towards the equilibrium COHb level corresponding to the present measurement sample.

14. The method as recited in claim 13, wherein the step of providing the warning signal includes activating an alarm when the COHb levels equals or exceeds a predetermined COHb level.

15. The method as recited in claim 14, wherein the predetermined COHb level is about 10%.

16. The method as recited in claim 13, further comprising the steps of:

periodically measuring an environmental methane concentration in the area; and activating an alarm if the methane concentration exceeds a predetermined concentration.

17. The method as recited in claim 13, further comprising the step of filtering other atmospheric gases using a hydrophobic zeolite filter.

* * * * *